(12) United States Patent
Keat et al.

(10) Patent No.: US 11,744,475 B2
(45) Date of Patent: *Sep. 5, 2023

(54) REMOTE HEART RATE MONITORING BASED ON IMAGING FOR MOVING SUBJECTS

(71) Applicant: RAPSODO PTE. LTD., Singapore (SG)

(72) Inventors: Kelvin Yeo Soon Keat, Singapore (SG); Batuhan Okur, Singapore (SG)

(73) Assignee: RAPSODO PTE. LTD., Singapore (SG)

( * ) Notice: Subject to any disclaimer, the term of this patent is extended or adjusted under 35 U.S.C. 154(b) by 608 days.

This patent is subject to a terminal disclaimer.

(21) Appl. No.: 16/883,961

(22) Filed: May 26, 2020

(65) Prior Publication Data

US 2021/0038096 A1 Feb. 11, 2021

Related U.S. Application Data

(63) Continuation of application No. 14/501,490, filed on Sep. 30, 2014, now Pat. No. 10,660,533.

(51) Int. Cl.

| | |
|---|---|
| *A61B 5/024* | (2006.01) |
| *A61B 5/00* | (2006.01) |
| *A61B 5/103* | (2006.01) |
| *G06T 7/00* | (2017.01) |
| *G06T 7/246* | (2017.01) |

(52) U.S. Cl.
CPC ...... *A61B 5/02416* (2013.01); *A61B 5/02427* (2013.01); *A61B 5/1032* (2013.01); *A61B 5/72* (2013.01); *A61B 5/721* (2013.01); *A61B 5/7207* (2013.01); *G06T 7/0016* (2013.01); *G06T 7/246* (2017.01); *A61B 5/725* (2013.01); *G06T 2207/10016* (2013.01); *G06T 2207/30076* (2013.01)

(58) Field of Classification Search
CPC ........ G06T 2207/30076; A61B 5/7207; A61B 5/721

See application file for complete search history.

(56) References Cited

U.S. PATENT DOCUMENTS

| | | | |
|---|---|---|---|
| 8,542,877 B2 * | 9/2013 | Jeanne | A61B 5/0255 382/128 |
| 8,977,347 B2 | 3/2015 | Mestha | |
| 9,185,353 B2 * | 11/2015 | Mestha | G06T 5/002 |
| 9,332,183 B2 | 5/2016 | Yano | |
| 9,998,749 B2 | 6/2018 | Urbach | |

(Continued)

*Primary Examiner* — Oommen Jacob
(74) *Attorney, Agent, or Firm* — Maschoff Brennan

(57) ABSTRACT

Systems and methods are disclosed to measure a PPG signal. In some embodiments, a method may include capturing a plurality of frames of a subject; tracking the position of a region of interest of the subject in each of the plurality of frames; creating a first time series signal, a second time series signal, and third time series signal corresponding with respective color channels of the plurality of frames; normalizing the first, second, and third time series signals, combining the normalized first time series signal, the normalized first time series signal, and the normalized first time series signal into a combined signal; creating a spectral signal from the combined signal; and extracting the PPG signal from the spectral signal.

13 Claims, 10 Drawing Sheets

(56) References Cited

U.S. PATENT DOCUMENTS

| | | |
|---|---|---|
| 10,028,669 B2 * 7/2018 | McDuff | A61B 5/02427 |
| 10,143,377 B2 * 12/2018 | Tsien | A61B 5/0077 |
| 2002/0154315 A1 10/2002 | Myrick | |
| 2008/0279436 A1 11/2008 | Razifar | |
| 2011/0040496 A1 2/2011 | Banerjee | |
| 2011/0251493 A1 * 10/2011 | Poh | G06V 10/7715 |
| | | 382/128 |
| 2012/0093214 A1 4/2012 | Urbach | |
| 2012/0236120 A1 9/2012 | Kramer | |
| 2013/0058525 A1 3/2013 | Sugio | |
| 2013/0135353 A1 5/2013 | Cobb | |
| 2013/0166294 A1 6/2013 | Cox | |
| 2013/0195373 A1 * 8/2013 | Shibata | G06K 7/1473 |
| | | 382/263 |
| 2013/0215244 A1 8/2013 | Mestha | |
| 2013/0218028 A1 8/2013 | Mestha | |
| 2013/0342670 A1 12/2013 | Kyal | |
| 2013/0343614 A1 12/2013 | Kyal | |
| 2013/0345568 A1 * 12/2013 | Mestha | A61B 5/02405 |
| | | 600/479 |
| 2013/0345569 A1 12/2013 | Mestha | |
| 2014/0037212 A1 2/2014 | Endo | |
| 2014/0088433 A1 3/2014 | Shan | |
| 2014/0221845 A1 8/2014 | Mestha | |
| 2014/0226900 A1 8/2014 | Saban | |
| 2014/0323888 A1 10/2014 | Kyal | |
| 2014/0376789 A1 12/2014 | Xu | |
| 2014/0378842 A1 * 12/2014 | Xu | A61B 5/0205 |
| | | 600/479 |
| 2015/0002518 A1 1/2015 | Nakajima | |
| 2015/0005646 A1 * 1/2015 | Balakrishnan | A61B 5/1128 |
| | | 600/479 |
| 2015/0043810 A1 2/2015 | Deng | |
| 2015/0190063 A1 * 7/2015 | Zakharov | A61B 5/14551 |
| | | 600/479 |
| 2015/0248223 A1 9/2015 | Krupnik | |
| 2015/0271329 A1 9/2015 | Deshmukh | |
| 2015/0320363 A1 11/2015 | De Haan | |
| 2016/0080192 A1 3/2016 | Stadelmeier | |
| 2016/0106328 A1 4/2016 | Mestha | |

\* cited by examiner

REMOTE HEART RATE MONITORING BASED ON IMAGING FOR MOVING SUBJECTS

FIELD

This disclosure relates generally to remote heart rate monitoring based on imaging for moving subjects.

BACKGROUND

Vital signs may generally include physiological statistics which indicate basic body functions of a living being. Vital signs are usually measured clinically. However, recent advancement in sensing and computing technology makes biomedical data like heart rate and breathing rate accessible to smartphone users. The monitoring of vital signs has gone beyond the scope of health care to security, sports performance enhancement, leisure, and many others. For example, pulse rate (in beats per minute or bpm) indicates the condition of one person in sports, sleep quality, stress level, and anxiety.

Currently, heart rate monitors may be used to measure pulse rate or pulse rate-derived metrics like heart rate variability (HRV) and blood oxygen saturation (SpO2). Most clinical heart rate monitors include chest straps, Holters, and ECG devices are contact-based measurement devices. They are not designed to be used by multiple users without changing or washing part of or the entirety of the device.

Current video remote heart rate measurement methods and remote photoplethysmograph methods involve taking continuous images and measuring the change in intensity of the subject face or limbs. Some methods require a subject to be still. This is because subject motion will introduce variation of light that is reflected off the surface of the area of interest. This variation of intensity, if falling within the frequency range of the periodic signal of interest to be measured, will decrease the signal-to-noise ratio and skew, affect the robustness, and/or affect the accuracy of the measurement.

The subject matter claimed herein is not limited to embodiments that solve any disadvantages or that operate only in environments such as those described above. Rather, this background is only provided to illustrate one example technology area where some embodiments described herein may be practiced.

SUMMARY

Systems and methods are disclosed to measure a PPG signal. In some embodiments, a method may include capturing a plurality of frames of a subject; tracking the position of a region of interest of the subject in each of the plurality of frames; creating a first time series signal, a second time series signal, and third time series signal corresponding with respective color channels of the plurality of frames; normalizing the first, second, and third time series signals, combining the normalized first time series signal, the normalized first time series signal, and the normalized first time series signal into a combined signal; creating a spectral signal from the combined signal; and extracting the PPG signal from the spectral signal.

In some embodiments, motion artifacts may be removed from the spectral signal prior to extracting the PPG signal from the spectral signal. In some embodiments, the combined signal may be filtered to exclude signals having a frequency less than 30 BPM and greater than 250 BPM.

In some embodiments, the method may include creating a first time series signal corresponding with a first color channel of the plurality of frames further comprises for each frame averaging each of the pixels within the region of interest corresponding with the first color; creating a second time series signal corresponding with a second color channel of the plurality of frames further comprises for each frame averaging each of the pixels within the region of interest corresponding with the second color; and creating a third time series signal corresponding with a third color channel of the plurality of frames further comprises for each frame averaging each of the pixels within the region of interest corresponding with the third color.

In some embodiments, each data point of the first time series signal, the second time series signal, and the third time series signal may be associated with a frame of the plurality of frames. In some embodiments, the method may further comprise determining a position of one or more points within the region of interest for each of the plurality of frames.

In some embodiments, the method may comprise determining a plurality of Euclidian distances between a position of a point within the region of interest within a given frame and each position of the point within the region of interest within each of a subset of frames of the plurality of frames; averaging the first color channel pixels within the region of interest of the frames of the plurality of frames associated with a Euclidean distance that is less than a threshold Euclidean distance to create an averaged first color channel value; and dividing the data value associated with the given frame of the plurality of frames by the averaged first color channel value.

In some embodiments, extracting the PPG signal from the spectral signal further comprises excluding motion artifact signals from the combined signal. In some embodiments, the method may include measuring the ambient light conditions; determining an ambient light correction based on the ambient light conditions; and correcting the first time series signal, the second time series signal, and the third time series signal using the ambient light correction.

In some embodiments the method may include determining acceleration data; and correcting for blur artifacts using the acceleration data.

A heart rate monitor is disclosed according to some embodiments described herein. The heart rate monitor may include a camera; an accelerometer; a memory; and a processor electrically coupled with the camera, the accelerometer, and/or the memory. The processor configured to perform all or parts of the method described above and/or any or all methods described herein.

These illustrative embodiments are mentioned not to limit or define the disclosure, but to provide examples to aid understanding thereof. Additional embodiments are discussed in the Detailed Description, and further description is provided there. Advantages offered by one or more of the various embodiments may be further understood by examining this specification or by practicing one or more embodiments presented.

BRIEF DESCRIPTION OF THE FIGURES

These and other features, aspects, and advantages of the present disclosure are better understood when the following Detailed Description is read with reference to the accompanying drawings.

DETAILED DESCRIPTION

Some embodiments described herein relate to a remote photoplethysmograph (PPG) heart rate monitor configured to measure breathing rate, pulse rate, and/or pulse rate-derived vital signs (hereinafter, "PPG signal" or "PPG"). Some existing remote heart rate monitor systems require a subject to stay perfectly still so not to introduce motion artifact in the measurement. These existing systems come in the form of mobile devices with an RGB camera. The capability of the system to measure the PPG signal of the subject in motion allows pulse rate reading to be incorporated into different applications like sports, well-being, security, and stress management.

An example embodiment includes a system that includes a camera. This camera system may capture continuous images of a subject for PPG signal measurement. The system may track a region of interest and convert the various pixels into time series signals for each channel and process the signal to extract a PPG and/or to find the pulse rate of the subjects. The PPG signals may be transmitted wirelessly or wired to a display device to give users feedback. The system may employ accelerometer-based motion blur removal and ambient light color measurement to correct for motion blur and ambient light color.

The PPG signal may include, but is not limited to, pulse rate, breathing rate, oxygen saturation, and heart rate variability, among many other signals. PPG signal may be measured on region of interest on cheeks, forehead, limbs, and other parts of the skin where volumetric changes of blood generate substantial variation in light absorbed.

Embodiments described herein may be used in a number of different contexts such as, for example, a treadmill maker may include the system as a peripheral to the treadmill system. The system may provide pulse rate to the user without requiring the user to put his hands on a metallic sensor rod or the user to bring his own chest strap heart rate monitor. The system may also be attached to a stationary bicycle or other fitness equipment serving the same purpose as when the system is attached to a treadmill. The heart rate feedback provided by the system may be used for instantaneous monitoring of the user's pulse rate as an indication of the user's well-being and the rigorousness of the exercise the user is undertaking. The heart rate feedback provided by the system may be used also for observation of long-term variation in pulse rate.

Figure 1:
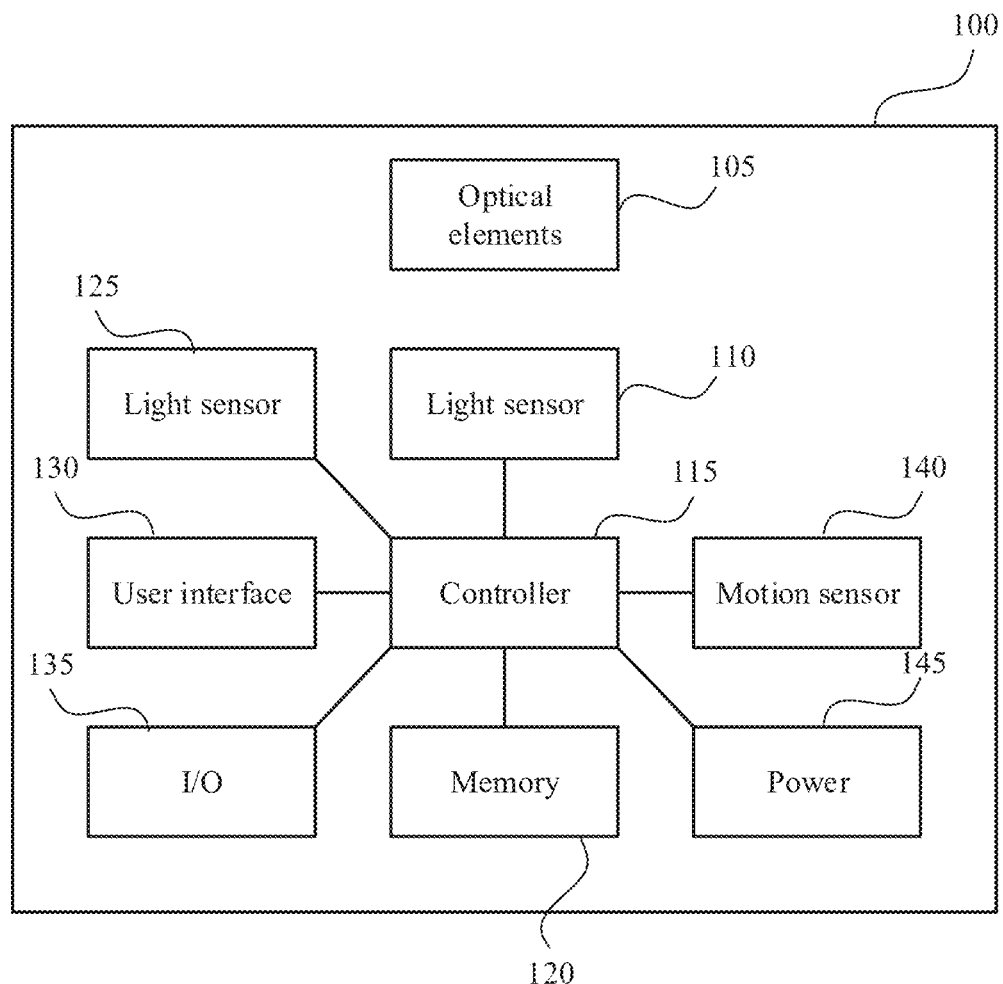
FIG. 1 illustrates a block diagram of an example heart rate monitor 100 according to some embodiments described herein.

FIG. 1 illustrates a block diagram of an example heart rate monitor 100 according to some embodiments described herein. The heart rate monitor 100 may include one or more optical elements 105, a light sensor 110, a controller 115, a memory 120, one or more ambient light sensors 125, a user interface 130, an input/output port 135, a motion sensor 140, and/or a power supply 145. The components may be connected wirelessly or via wired connections. Moreover, various components may be communicatively coupled together with and without the controller 115.

The one or more optical elements 105 may include lenses, filters, polarizers, shutters, prisms, mirrors, etc. The one or more optical elements 105 may be disposed to collect light from a target and focus the light to the light sensor 110.

The light sensor 110 may include an RGB light sensor 110 such as, for example, a CCD sensor or CMOS sensor. The light sensor 110 may produce signals representing the intensity of light incident on a given pixel. The light sensor 110 may also produce a three-channel, time-varying signal. The three channels represent each of the RGB color channels. In some embodiments, the light sensor 110 may be an infrared camera with a spatial separation filter that filters the reflected light into two or more channels.

The controller 115 may be configured to execute computer instructions stored in the memory 120 that cause the controller 115 to perform the functions and operations described in the computer instructions. The controller 115 may include, but is not limited to, a processor, a microprocessor ($\mu P$), a controller, a microcontroller ($\mu C$), a central processing unit (CPU), a digital signal processor (DSP), a multicore processor, any combination thereof, or other suitable processor. Computer instructions may be loaded into the memory 120 for execution by the controller 115. For example, the computer instructions may be in the form of one or more modules.

The controller 115 may perform many tasks such as, for example, those with real-time constraints. For instance, the controller 115 may track the region of interest from one frame to the other by measuring the 6 degrees of freedom and locating a pixel coordinate where the vertices enclosing the region of interest are located. The controller 115 may also perform normalization based on the current and past coordinates of the subject. In some embodiments, the controller 115 may also calculate the point spread function (PSF) from the accelerometer output to de-blur the image. The controller 115 may also combine the normalized R, G, and B values to chrominance value to minimize motion artifact, band pass filter the chrominance series in time, and find the spectral components in the chrominance signal. The controller 115 may find the peak on the spectral plot that is closest to the heart rate by comparing chrominance spectral plot and motion artifact spectral plot which is derived from performing FFT on the motion channel.

Figure 10:
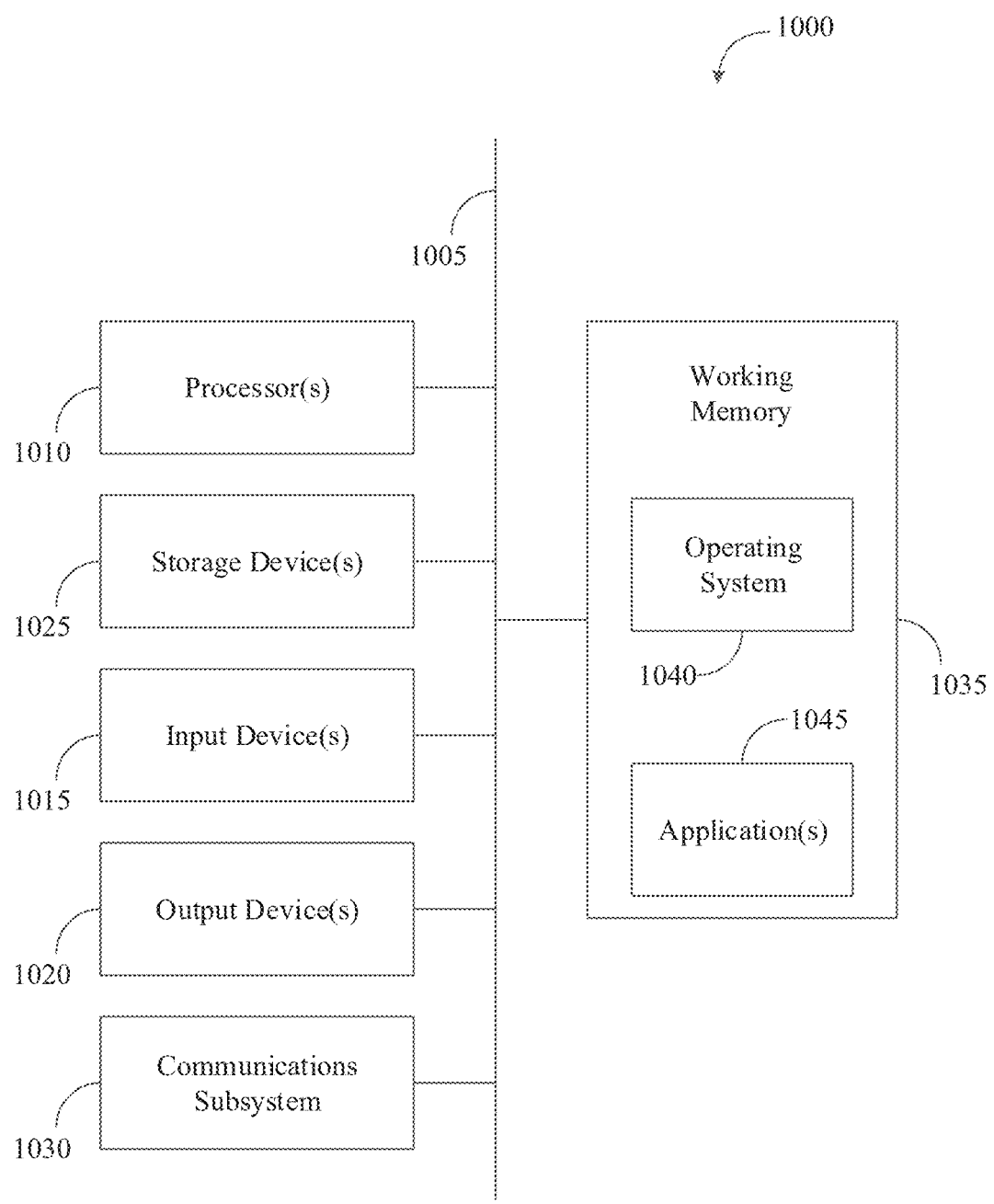
FIG. 10 shows an illustrative computational system for performing functionality to facilitate implementation of embodiments described herein.

The controller 115 may include any or all of the components described in conjunction with FIG. 10 such as, for example, a processor 1010. Moreover, the memory 120 may include storage devices 1025 shown in FIG. 10.

The memory 120 may include any type of electronic storage media. In some embodiments, data generated, received, and/or operated on during performance of the functions and operations described herein may be at least temporarily stored in the memory 120. Moreover, the memory 120 may include volatile storage such as RAM. The memory 120 may include a non-transitory computer-readable medium such as, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory computer-readable medium.

The ambient light sensors 125 may include the RGB light sensor 110 such as, for example, a CCD sensor or CMOS sensor. The light sensor 110 may produce signals representing the intensity of light incident on a given pixel. The light sensor 110 may also produce a three-channel, time-varying signal. The three channels represent each of the RGB color channels. The ambient light sensors 125 may measure the color of ambient light for various purposes such as, for example, for white light normalization. In an alternative embodiment, the heart rate monitor 100 may not include an ambient light color sensor. Instead the heart rate monitor 100 may use a white balance correction algorithm to normalize non-white incident light.

The user interface 130 may include any type of user interface such as, for example, a keyboard, a screen, a touch screen, a pointer device, one or more buttons, LED lights, displays, screens, etc. In some embodiments, the user interface 130 may be located remotely relative to the heart rate monitor 100 and/or may communicate with the heart rate monitor 100 wirelessly. In some embodiments, the user interface 130 may be part of another device such as a smartphone, tablet, computer, etc.

The input/output port 135 may include any type of data communication port such as, for example, a serial data port (e.g., USB), Bluetooth, Wi-Fi, etc.

The motion sensor 140 may include, for example, an accelerometer, a gyroscope, and/or a magnetometer. The motion sensor 140 may include, for example, a nine-axis sensor that outputs raw data in three axes for each individual sensor: acceleration, gyroscope, and magnetometer, or it can output a rotation matrix that describes the rotation of the sensor about the three Cartesian axes. Moreover, the motion sensor 140 may also provide acceleration data. The motion sensor 140 may be sampled and the motion data saved into the memory 120. Alternatively, the motion sensor 140 may include separate sensors such as a separate one-, two-, or three-axis accelerometer, a gyroscope, and/or a magnetometer. The raw or processed data from these sensors may be saved in the memory 120 as motion data.

The power supply 145 may include any component that can provide power to the various circuits, components, devices, memories, light sensors, motion sensors, etc. For example, the power supply may include a battery, a rechargeable battery, and/or an AC/DC converter that can be connected with an AC power source.

The heart rate monitor 100 may be placed in any configuration that allows the subject's region of interest to be within the field of view of the imager, the region of interest size is sufficiently large for good signal-to-noise ratio (SNR), and/or the subject is well illuminated with a stable light source. For example, in some alternative embodiments, the heart rate monitor 100 may be configured to operate with a consumer entertainment product like a TV, game console, or any other environment in which measurement of pulse rate is required.

Figure 7:
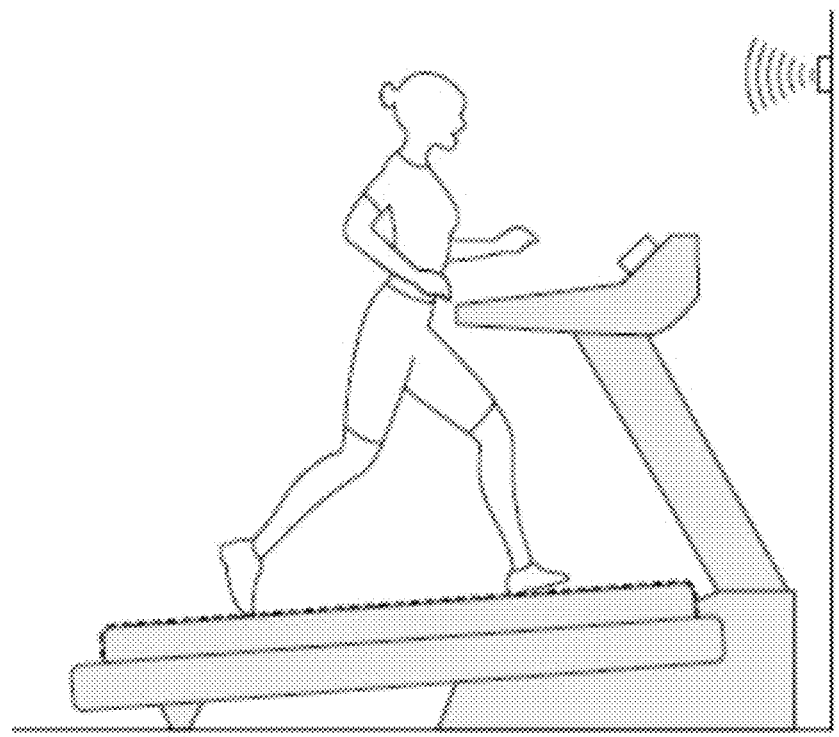
FIG. 7 illustrates a heart rate monitor coupled with a treadmill according to some embodiments described herein.
Figure 8:
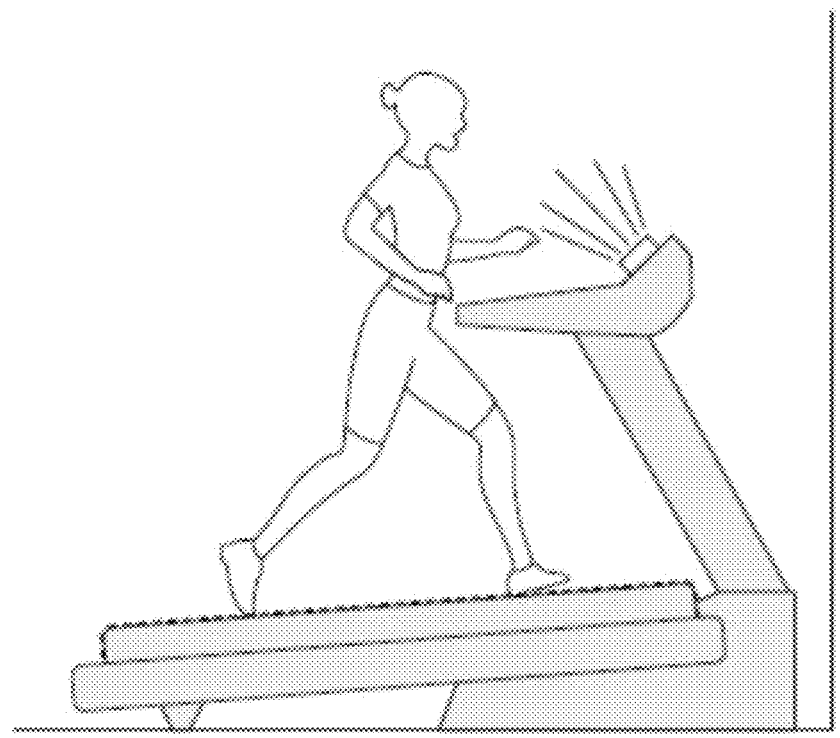
FIG. 8 illustrates a heart rate monitor coupled with a treadmill according to some embodiments described herein.

FIG. 7 illustrates an example of the heart rate monitor 100 positioned on a treadmill according to some embodiments described herein. FIG. 8 illustrates another example of the heart rate monitor 100 positioned on a treadmill in a different configuration according to some embodiments described herein. In both FIG. 7 and FIG. 8, the subject may be running on a treadmill. The operating environment is not limited to gym equipment. In both FIG. 7 and FIG. 8, the heart rate monitor 100 and/or the user interface 130 of the heart rate monitor 100 can be attached to the treadmill.

The user interface 130 may display the measurement from the system, give the user feedback on the readiness of the measurement, and/or other user-related feedback that may or may not involve the measurement from the system. The heart rate monitor 100 may transmit the measurement to a separate device wirelessly or wired. In an alternative embodiment, the heart rate monitor 100 may be separated from the treadmill and mounted on the wall to eliminate motion blur due to the movement of the treadmill due to the force exerted by the user on the treadmill. In this alternative embodiment, the heart rate monitor 100 may transmit the pulse rate wirelessly to the treadmill. In some embodiments, the heart rate monitor 100 may be attached to a tripod to get the best field of view that captures the region of interest of the subject regardless of the subject's motion.

Figure 9:
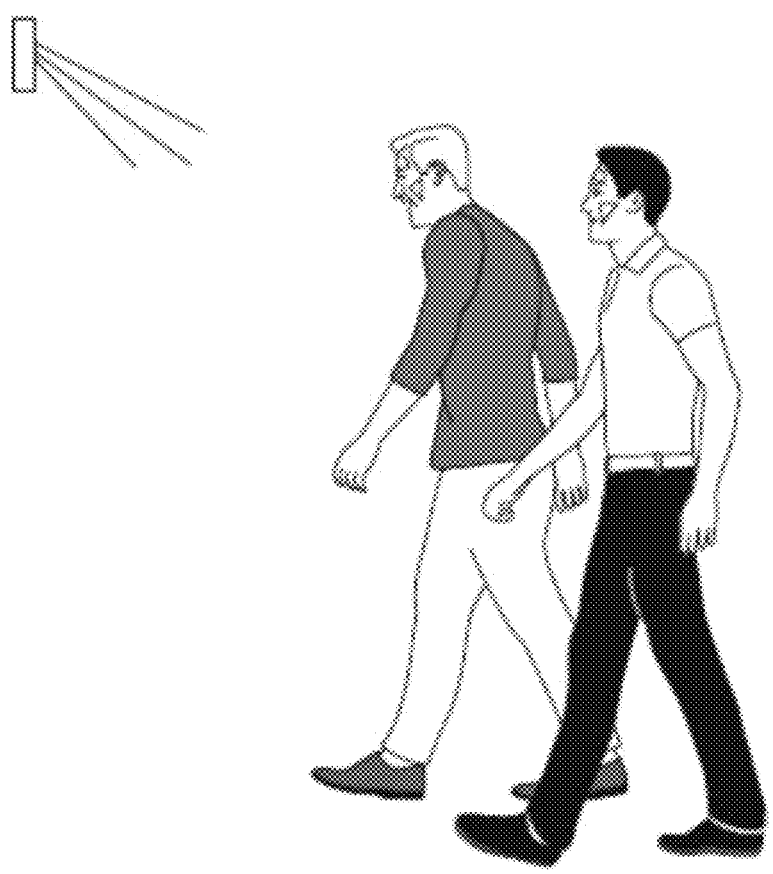
FIG. 9 illustrates a heart rate monitor disposed within a passageway according to some embodiments described herein.

FIG. 9 illustrates an example of the heart rate monitor 100 at a set location to read the heart rate of individuals or a group of individuals in a hallway, a crowd, a passageway, at a desk, etc. For example, the heart rate monitor 100 may be positioned to measure the heart rate of an individual to determine stress level, which can be a function of heart rate. This may be useful, for example, in monitoring employee behavior, at security check points, at airports, etc. In some embodiments, the heart rate monitor 100 may measure the pulse rate of multiple users in the same frame as long as these users have a PPG region of interest in the field of view of the camera.

Various embodiments are described in reference to a subject. These references can be expanded to more than one subject. Moreover, any reference to a region of interest may be expanded to multiple regions of interest. Further, any reference to a single frame may extend to multiple frames. Furthermore, any reference to a signal or a channel may extend to multiple signals or multiple channels.

Figure 2:
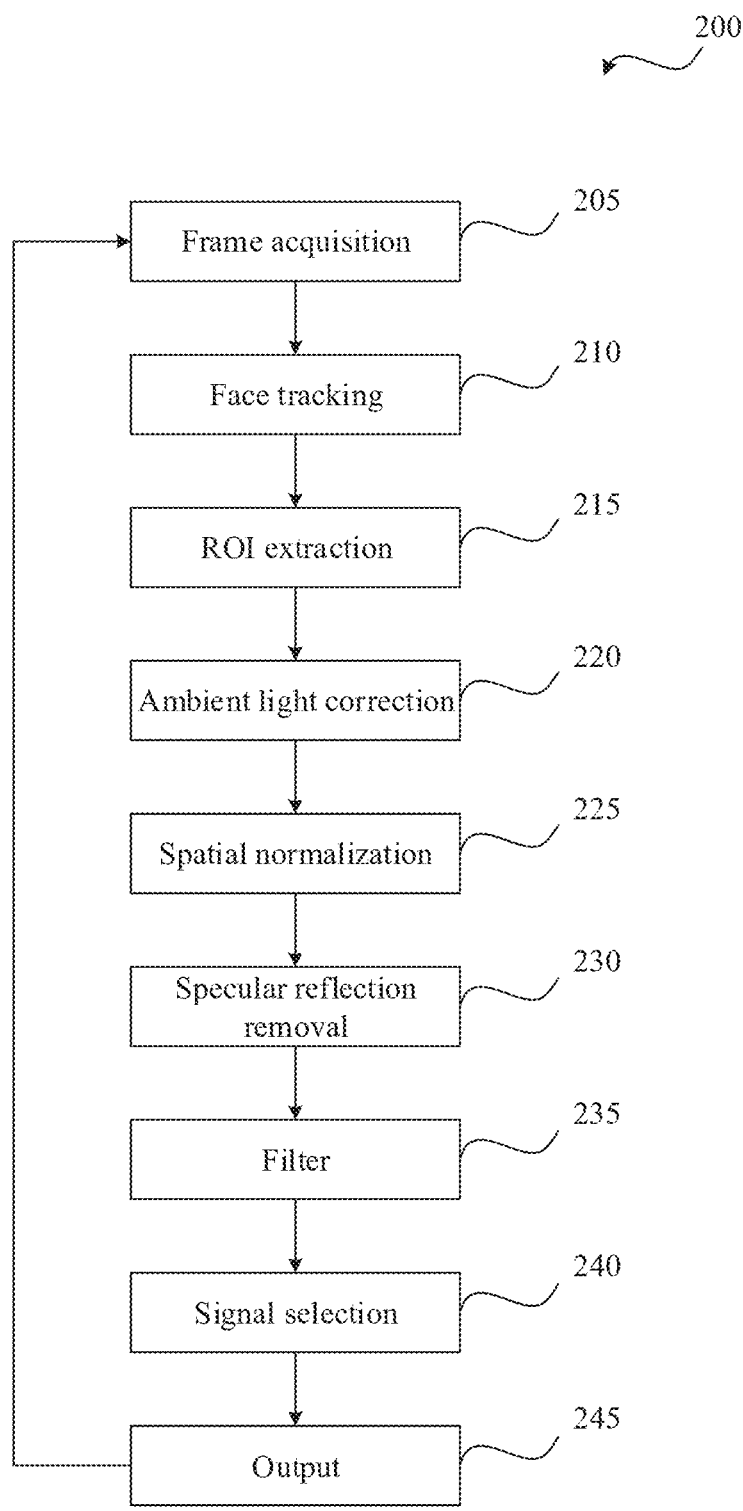
FIG. 2 is a flowchart of an example process 200 of determining the heart rate of a subject according to some embodiments described herein.

FIG. 2 is a flowchart of an example process 200 of determining the heart rate of a subject according to some embodiments described herein. One or more steps of the process 200 may be implemented, in some embodiments, by one or more components of the heart rate monitor 100 of FIG. 1. Although illustrated as discrete blocks, various blocks may be divided into additional blocks, combined into fewer blocks, or eliminated, depending on the desired implementation.

In some embodiments, one or more blocks of the process 200 may be repeated continuously to derive the heart rate from the subject. For example, each block may be used to act on a single frame of a plurality of frames and the process 200 may repeat in order to act on multiple frames.

At block 205 a frame that includes an image of a subject may be acquired. The frame may be one of many frames acquired by the light sensor 110.

At block 210 the subject's face in the frame may be tracked in a two- or three-dimensional space. The face may be tracked, for example, by identifying and tracking one or more features (or blips) in each frame that a tracking algorithm can lock onto and follow from previous frames to the current frame. The features may include various facial recognition features such as portions or all of eyes, ears, noses, mouths, nostrils, the corners of the lips, corners of the eyes, wrinkles, etc. Tracking algorithms may use, for example, template matching based on NCC score and/or RMS error. Each feature, for example, may represent a specific point on the surface of the subject's face. As the feature is tracked, it becomes a series of two-dimensional coordinates that represent the position of the feature across a series of frames. This series can be referred to as a "track." Once tracks have been created they can be used immediately for 2-D motion tracking, or then be used to calculate 3-D information.

In some embodiments, the face may be tracked using one or more algorithms such as, for example, target representation, localization algorithms, and/or filtering and data association algorithms. Furthermore, target representation and localization algorithms may include, for example, blob tracking, kernel-based tracking, contour tracking, visual feature matching, and/or particle filter tracking.

In some embodiments, a face tracker module may be used at block 210. In some embodiments, the face tracker module may receive as an input data specifying one or more sets of vertices that define one or more regions of interest to be tracked on the one or more subject's faces. For example, the input may include data defining the vertices of a polygon (e.g., triangle, square, rhombus, rectangle, polygon, etc.) specifying an area on a subject's left cheek, right cheek, and/or forehead or any other location on the subject's body. In some embodiments, a quadrilateral fit on one or more cheekbones may define the region of interest. In this embodiment the vertices are the corners of the quadrilaterals.

In some embodiments, a face tracker module may be used at block 210. In some embodiments, the face tracker module may output motion data that specifies the six degrees of freedom of the subject's (or subjects') face(s). This data may include the location of the face such as, for example, the location of the face in space in Cartesian coordinates (e.g., x, y, z) and/or pixel coordinates in two-dimensional space; as well as rotation data (e.g., yaw, pitch, and roll). In some embodiments, the face tracking may be implemented by a facial features tracking engine (a facial motion capture engine).

In some embodiments, the pixel coordinates of three or more vertices enclosing the region of interest may also be identified and tracked in the frame in conjunction with a plurality of previous frames using light coding techniques. Light coding techniques, for example, may use an infrared projector (e.g., an infrared laser projector) and/or camera and a special microchip to track the movement of a subject's face in three dimensions.

In some embodiments, color mapping may be used to locate the region of interest in one frame and/or to track the region of interest from one frame to another. In some embodiments, each region of interest may first be checked for occlusion by facial hair, other body parts, or external objects. Any occluded or obstructed pixels may be ignored.

Moreover, in some embodiments, each region of interest may be checked for out-of-frame occurrences. If some of the pixels of a region of interest are out of frame, these pixels may be ignored. Alternatively or additionally, if some of the pixels of a region of interest are out of frame, all the pixels in the region of interest may be ignored.

In some embodiments, at block 210 the pixel locations of vertices defining one or more regions of interest in the current frame may be output and/or saved in the memory 120. Alternatively or additionally, at block 210 the motion data specifying the six degrees of freedom of the subject's face in the current frame may be output and/or saved in the memory 120.

At block 215 the pixels associated with the region of interest on the subject's face can be extracted and converted into three different color-based data points representing a given frame according to some embodiments described herein. For example, the pixels within the vertices defining the region of interest associated with the blue channel of the Bayer filter may be averaged and returned as the blue channel data point for the frame. The pixels within the vertices defining the region of interest associated with the green channel of the Bayer filter may be averaged and returned as the green channel data point for the frame. The pixels within the vertices defining the region of interest associated with the red channel of the Bayer filter may be averaged and returned as the red channel data point for the frame.

Figure 3:
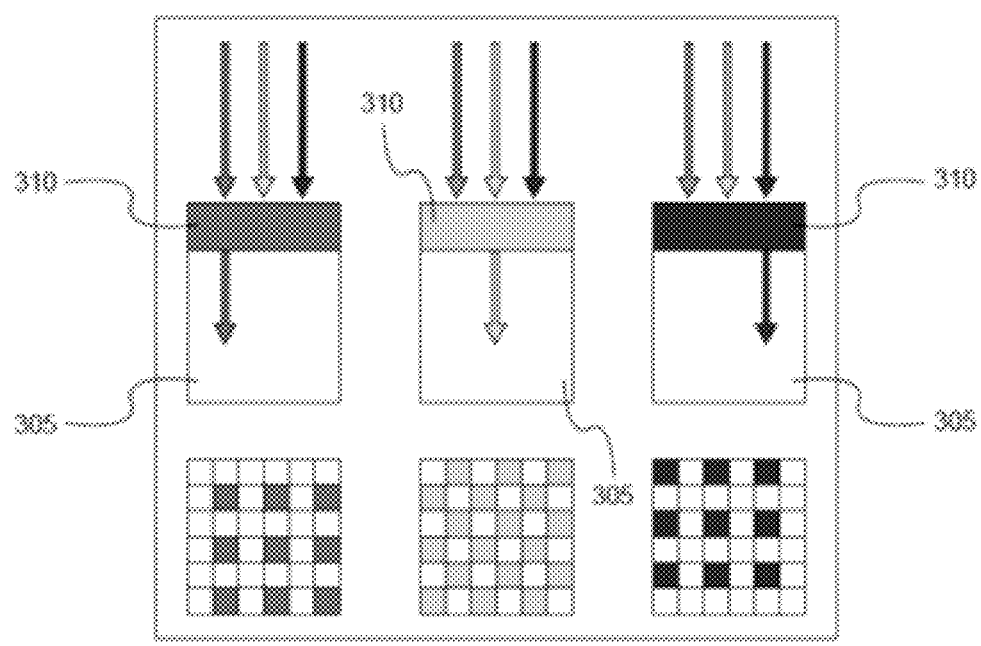
FIG. 3 illustrates an example Bayer filter according to some embodiments described herein.

For example, the blue channel data point for the frame, the red channel data point for the frame, and the green channel data point for the frame can be averaged through a binning process. As shown in FIG. 3, each pixel 305 of the imager may be associated with a different mosaic of a color filter 310 that filters different wavelengths of light. This filter may be a Bayer filter. Each pixel may only sense light associated with the color of the given mosaic of the color filter 310. The raw output of Bayer-filter cameras may be referred to as a Bayer pattern image. Since each pixel is filtered to record only one of three colors, the data from each pixel cannot fully specify each of the red, green, and blue values on its own. To obtain a full-color image, various demosaicing and/or interpolation algorithms can be used to interpolate a set of complete red, green, and blue values for each pixel. These algorithms make use of the surrounding pixels of the corresponding colors to estimate the values for a particular pixel.

In some embodiments, an image can be received from the RGB camera and may not be converted to a full three-channel image and/or may not be interpolated. Instead, in some embodiments, the pixels within the region of interest may be separated into the three bins associated with the Bayer filter. For example, if the pixel measures red light only, the pixel will be included in the R bin, if the pixel measures green light only, the pixel will be included in the G bin, and if the pixel measures blue light only, the pixel will be included in the B bin. The average value of each bin may be returned as the channel data point for the frame.

The channel data points for each of the red, green, and blue channels may be calculated for each frame and three time-varying signals may be created. Each data point of each time-varying signal may represent the average value of the channel for the region of interest. Using the RGB light sensor 110 with a Bayer filter, block 215 may return three-channel data points. These three-channel data points may each be appended at block 215 or some later block, to three-channel data signals. The channel data signals may comprise channel data points associated with each of the previous frames.

At block 220 ambient light corrections can be performed on the channel data points according to some embodiments described herein. Ambient light correction can occur in any number of ways.

In some embodiments, the ambient light illuminating the subject may vary over time or vary based on location and/or implementation. For example, the ambient light may include fluorescent lights located in a gym, sunlight from a window that changes throughout the day, light produced by the heart rate monitor 100, a flashlight module that is synchronized with the light sensor 110, etc. Moreover, the ambient light may not produce white light, which may result in one channel of the three time-varying signals having greater value than it should.

In some embodiments, the ambient light correction may include white balance correction, a color balance correction, etc. In some embodiments, an ambient light sensor may be used to perform ambient light corrections.

In some embodiments, the ambient light sensors 125 may include an array of red, green, and blue sensors. In some embodiments, the various different sensors may be coated with different material having different light efficiency. The blue sensor may allow more light in the blue color spectrum to pass through, and likewise for the green sensor with green color light and the red sensor with red color light. The output of the ambient light sensors 125 may include three values representing the red, green, and blue light intensity incident on the sensors. For the application of colored light equalization, the absolute value of the output of the ambient light sensor 125 may not be as useful as the relative value of the output of the ambient light sensor 125. The color of the incident light may be measured and used to determine the ratio of the light in the three channels. A white light, for example, may have equal intensity in the red, green, and blue channels. Under the dichromatic reflection model, the specular reflection may be a function of incident light and/or the angle of reflection. If the incident light on the three channels is equalized, the specular reflection component, which is a part of motion artifact, can be equalized. The elimination of specular reflection-induced motion artifact now becomes a problem of subtraction of one channel signal to the other.

In some embodiments, the ambient light sensor may be calibrated to equalize the quantum efficiency difference between the ambient light sensor and the camera chip sensor. Due to difference in material used, the red, green, and blue light efficiency of both sensors may be different. Under the same light, the red-over-green ratio for camera chip and the ambient light color sensor will be different. In some embodiments, the measurement from the ambient light color sensor is used to calibrate the light color of the incident light on the camera sensor. In the current system, the calibration of both sensors is done by finding the area under the quantum efficiency plot of red, green, and blue light for both sensors. The ratio of this value represents the ratio that the sensors will read when a white light is shining on both sensors. For every subsequent measurement on both camera sensor and light sensor the value may be divided by normalization value which is the area under red, green, and blue quantum efficiency plot. In an alternative embodiment, the system may perform light color equalization by performing white balance correction algorithm.

Thus, block 220 may return the three-channel data points with a correction for ambient light.

At block 225 a spatial normalization on the current frame's channel data point may be performed. In some embodiments, the spatial normalization may normalize the channel data points for the current frame based on the average value of previous frames associated with a position data that is close to the position data of the current frame. For example, the spatial normalization may be performed to equalize the changing intensity value of the pixels in the region of interest due to changes in the distance between the light source and the region of interest as the subject is moving.

For example, the Euclidean distance between the face in the current frame and the face in each of the previous frames or a subset of the previous frames may be determined. As another example, the Euclidean distance between each of the vertices of each region of interest in the current frame and each of the vertices of each region of interest in each of the previous frames or a subset of the previous frames may be determined.

The Euclidian distance may be calculated from the position data provided in block 210. The Euclidean distance may be calculated from the Cartesian coordinates of the position data using any algorithm or calculation that determines the distance between two points. The channel data point for each frame where the Euclidean distance is below a threshold value may be averaged to create three separate average spatial values. In some embodiments, the threshold value can be determined adaptively to ensure there are at least N points in the bins. These average spatial values may be used to spatially normalize the channel data point by dividing the channel data point for the current frame by the average spatial value to create a three-normalized-channel data point for each channel.

At block 230 the signal may be corrected for specular reflections. The channel data signals may include the time varying PPG signal and a time-varying motion-spatially dependent specular reflection signal. To eliminate the time-varying motion-spatially dependent specular reflection signal, the normalized channel data point may be combined using a weighted sum. For example, the weighted sum may include calculating the chrominance level from the YCbCr. Alternatively or additionally, the weighted sum may subtract one or more channels from another, add one or more channels together, divide one or more channels, multiply one or more channels, and/or any combination thereof.

For example, the weighted sum may include the difference of the normalized average blue data and the normalized average green data divided by the difference of the normalized average blue data and the normalized average red data. As another example, the weighted sum may include the difference of the normalized average blue data and the normalized average red data divided by the difference of the normalized average blue data and the normalized average green data. As another example, the chrominance of the normalized channel data point may be used.

The result of block 230 may provide a single data point for each frame that is the combined normalized channel data point.

Each combined normalized channel data point may be calculated for each frame and appended to a channel data signal that is a time-varying signal of the combined normalized channel data points.

At block 235 various filters can be applied. For example, the combined channel data signal may be band pass filtered to retain signals within an expected range for PPG signals in frequency. For example, any signal components with a frequency outside of the normal frequency of PPG signals such as, for example, 30-250 bpm may be filtered away using a band pass filter.

At block 240 the PPG signal may be extracted from the combined channel data signal. To extract the PPG signal from the combined channel data signal a Fast Fourier Transform (FFT), for example, may be performed on the combined channel data signal, for example, to create a spectral signal. From the spectral signal, the highest peak in the frequency axis may be selected as the PPG signal in Hz. In some embodiments, the frequency may be converted from Hz to beats per minute.

In some embodiments, motion data may be used to eliminate motion artifacts in the frequency domain prior to selecting the PPG signal. The motion data collected from the face tracking in block 210 may be used to determine the frequency of any motion of the subject over time. This motion data may include, for example, periodic motion while the subject walks or runs. The frequency of this motion data may be used to eliminate signals having the same frequency as this motion data. For example, peaks in the spectral signal that correlate with motion data may be given less weight than other signals when choosing for the best periodic component that best describe the PPG signal.

At block 245 the PPG data or the PPG signal may be output. For example, the PPG signal may be output to a user through the user interface 130. As another example, the PPG signal may be output through the input/output port 135.

Figure 4:
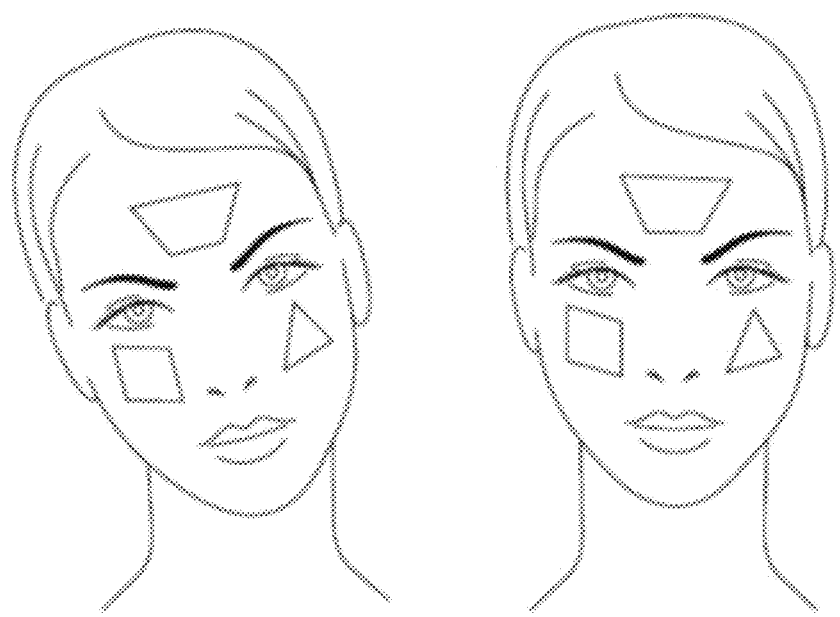
FIG. 4 illustrates the position of three different regions of interest according to some embodiments described herein.

FIG. 4 illustrates the position of three different regions of interest according to some embodiments described herein. The regions of interest may be tracked as discussed above in block 215 of the process 200 shown in FIG. 2. In some embodiments, one of the cores of a multicore controller 115 may be used (e.g., dedicated) to perform face and/or region-of-interest tracking. Three regions of interest are shown in the figure: left cheek, right cheek, and forehead. Each of these regions of interest may be defined by the vertices.

Figure 5:
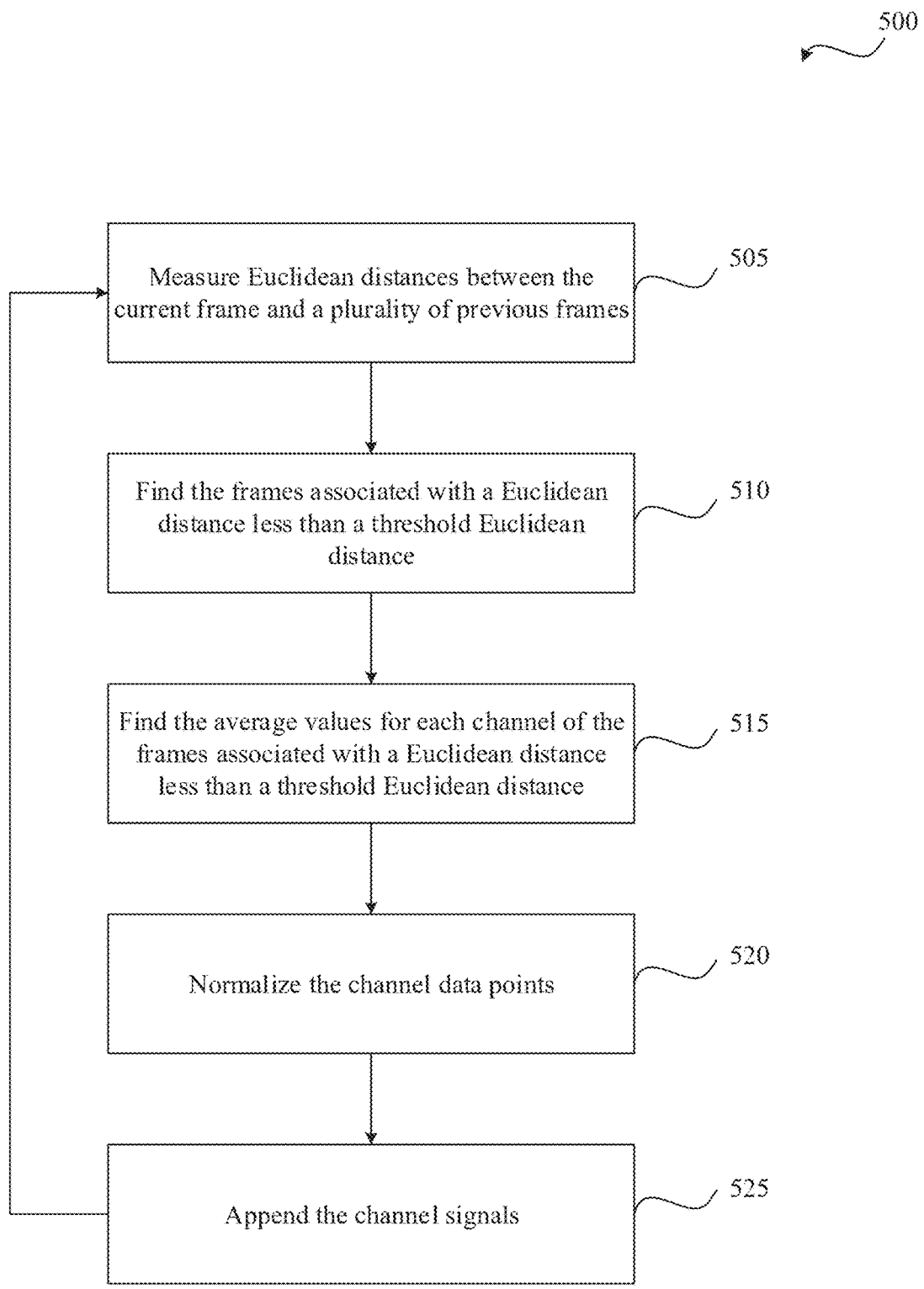
FIG. 5 is a flowchart of an example process 500 of a spatial normalization process according to at least one embodiment described herein.

FIG. 5 is a flowchart of an example process 500 of a spatial normalization process according to at least one embodiment described herein. One or more steps of the process 500 may be implemented, in some embodiments, by one or more components of the heart rate monitor 100 of FIG. 1. Although illustrated as discrete blocks, various blocks may be divided into additional blocks, combined into fewer blocks, or eliminated, depending on the desired implementation.

In some embodiments, the objective of normalization may be to equalize the value in time to offset the effect of intensity difference due to variations in the position of the subject in space.

At block 505, the Euclidean distance between a point (e.g., one vertex of a region of interest) in a frame and the point in N previous frames may be determined. Each point, for example, may include spatial coordinates as well as R, G, and B intensity information. In some embodiments, the vector for the Euclidean distance measurement may include two-dimensional coordinate pairs of three vertices or six degrees of freedom motion data. In some embodiments, other distance metrics such as, for example, hamming distance may be used instead of Euclidean distance.

At block 510, the channel data points for the M frames that correspond to a Euclidean distance below a threshold value may be used to determine the normalization value for the current frame's channel data. In some embodiments, the channel data points associated with a Euclidean distance below the threshold value may be clustered into data bins associated with each channel.

At block 515, the channel data points of the closest M frames found in block 510 may be averaged to give the normalizing factor. This normalizing factor, for example, may be a spatial-dependent parameter. In some embodiments, a unique normalizing factor may be determined for each channel. For example, a blue channel normalizing factor, a red channel normalizing factor, and a green channel normalizing factor.

At block 520, each of the current frame's channel data points may be divided by the normalizing factor or the channel normalizing factor. Averaging may eliminate the fast-changing distortion like noise and also the PPG signal in the normalizing factor measurement.

At block 525, in some embodiments, the current frame's channel data points may be appended to the array of past points for spatial normalization of the next point. In some embodiments, where the subject is small moving, spatial normalization is similar to time normalization because the movement is small within a time window that the points are close in space. The past points may not be recorded for spatial normalization for all the past data and only those in the time window is needed.

The process 500 may repeat by returning to block 505. The process may be repeated for each frame and/or each region of interest within a given frame.

Figure 6A:
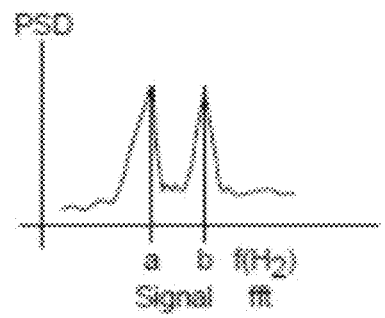
FIGS. 6A, 6B, and 6C illustrate an example of peak selection method on the spectrum of the signal processing output according to some embodiments described herein.
Figure 6B:
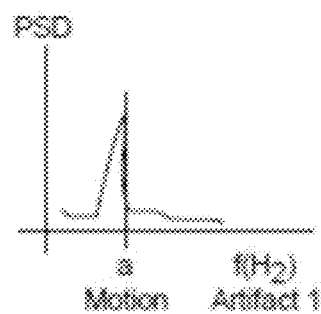
Figure 6C:
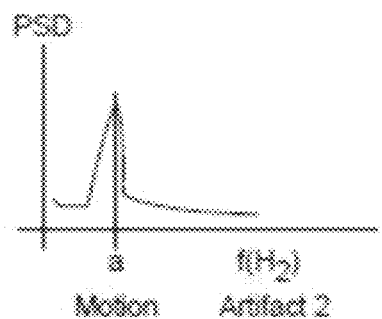

FIGS. 6A, 6B, and 6C illustrate an example of peak selection method on the spectrum of the signal processing output according to some embodiments described herein. Each plot in FIGS. 6A, 6B, and 6C is a plot of the frequency spectrum of the processed time series signal in the scenario of a motion artifact. In the absence of motion artifact, the strongest periodic component is the pulse rate. In the event there is a motion artifact, however, the peak that represents the motion artifact may be significantly high in the frequency spectrum. Motion artifact in PPG signal measurement is highly correlated to motion. The peak in the normalization output that corresponds to motion is usually located where the absolute peak is located in the frequency spectrum of the motion data.

In FIG. 6A, for example, the peak from PPG signal and peak from the motion artifact is similar in strength; the location of the absolute peaks of motion artifact frequency spectrum may be used to decide which peak is from the PPG signal. In FIG. 6A the peak shows up in both the plots in FIG. 6B and FIG. 6C of the motion data. It can be inferred that peak b represents the PPG signal.

The motion data of the face (e.g., the x, y, z roll, pitch, and yaw data) of the face may be used individually as motion data. In some embodiments, a windowing method may be performed on the frequency domain signal. The size of this window may be experimentally determined due to the limitation of how fast PPG signal can vary within a time window. This allows more informed decision making in terms of peak selection.

In some embodiments, the motion data may be used to predict the trend of the pulse rate changes. When a subject is accelerating, it can be deduced that the subject pulse rate will either remain still or increase in time. When a subject is slowing down, it can be deduced that the subject pulse rate will not increase by a big margin. The window where the PPG data may be found may change in conjunction with the increase or decrease in trends of the motion data.

In some embodiments, motion artifacts in the most common scenarios may not be a time-dependent parameter, but motion artifacts may be a space-dependent variable. For example, motion artifacts may depend on the x, y, z roll, pitch, and yaw of the region of interest. Different tilt of the subject region of interest may see different reflected light profile of the skin surface.

In some embodiments, the heart rate monitor 100 may be coupled with a treadmill as shown in FIGS. 7 and 8, and the subject may be running on the treadmill during measurement. This may introduce vibration on the treadmill and the heart rate monitor 100. In some embodiments, acceleration data may be used to correct for motion data in the spectral signal. The subject and the background may be blurred if the subject is moving very fast and the vibration is severe. This may cause dip in accuracy in tracking algorithm and PPG measurement.

To correct for the motion sensor 140, some embodiments may provide three-axis acceleration data (e.g., x, y, and z axes acceleration). The instantaneous velocity in one or more of the axis may be calculated from the acceleration readings. In some embodiments, the velocity in x, y, z roll, pitch, and yaw axes may be used to generate a spatially-invariant blurring kernel for every frame. This kernel may be used to perform de-blurring in the non-blind deconvolution step. In some embodiments, blind deconvolution may be performed on the raw image without having to know the motion of the system and the subject.

In some embodiments, if the ambient light that illuminates the subject is in a fixed position and has a stable light efficiency, spatial normalization on the R, G, and B signals will offset the changing intensity in each channel due to the changing of relative distance between subject to the light source. The light source in this case is a generic term that includes all factors that direct incident light to the region of interest surface. The average R, G, and B of frames n, m, and q are measured to exclude the PPG signal which is a periodic signal. The longer the measurement is, the more points may be taken for spatial normalization, the more accurate the normalization is. The underlying theory is that the light profile on the region of interest of the subject in frame q will be closer to the light profile on the region of interest of the subject in frames n and m than the subject in frames a, b, and c because of the proximity of space coordinate of q with n and m which is measured by taking Euclidean distance E of vector q with vectors n, m, a, b, and c. In the current system, the spatial normalization is performed during measurement when the subject is in motion. The accuracy and reliability of normalization of the signal at point q improves if there are closer points n and m to choose from to perform spatial normalization. In an alternative embodiment, a no-measurement initialization stage is introduced to collect enough spatial points for normalization. The subject is required to perform calibration step of moving around the origin to accumulate enough points for normalization. After enough points are acquired, the subject may start measurement.

In some embodiments, systems and methods are disclosed for remotely measuring and/or sensing PPG data from a human that is in motion such as, for example, while running on a treadmill. Embodiments described herein may include devices and/or methods for extracting a plurality of frames of color images of a human's face (or other skin areas) and tracking one or more regions of interest on the face. Three RGB time-based signals may be created where each value of the respective RGB time-based signal represents the respective color pixels within the region of interest for each frame. Each value of the time-based signals may be corrected for ambient light conditions and/or spatially normalized. Specular reflection artifacts may be used by a weighted sum. The summed signal may then be filtered and the spectral component may be selected as the PPG signal.

In some embodiments, region of interest may include the right cheek, the left cheek, and/or the forehead and may be tracked for every frame. The tracker may return the individual image coordinates of the vertices of the region of interest and also the six degrees of freedom motion with respect to an arbitrary origin. A time series channel data point for each color—red, green, and blue—and for each frame may be extracted by summing (or averaging) all the pixels within the region of interest. A channel data point for each channel may then be normalized spatially to eliminate the intensity difference within the channel due to the location of the region of interest in 3-D space. The normalized channel data points for each channel may be further normalized to correct for the color of ambient light hitting on the surface of the region of interest.

In some embodiments, an ambient light color sensor is used to measure the color of the ambient light. The normalized R, G, and B values together with the coordinates of the region of interest vertices and six degrees of freedom motion may be stored into the memory 120 for the normalization of subsequent frames. The R, G, and B values may be weighted summed to eliminate motion artifact. In some embodiments, the YCbCr chrominance is used. The ratio of Cb over Cr is used as the output time series. The highest peak in the spectrum represents the pulse rate of the subject in beats per minute (BPM).

Some benefits of the example embodiment and the other embodiments described herein may include a non-contact pulse rate measurement which allows switching between multiple users without changing part of or the entire system. The system allows the subject to not have motion restricted because of the electrodes, strap, etc. that are attached to the subject. Additionally, the benefits may include measuring pulse rate of the subject in motion. In previous embodiments in the domain of remote PPG measurement, the subject has to be perfectly still to eliminate the variation of intensity value of each pixel due to the position of the region of interest. This allows application in new domains like security, fitness and well-being equipment, safety, gaming, and other consumer electronic products. The benefit of the system may also include the small size and the simplicity of the system compared to systems in past embodiments that measure PPG signal of the subject in motion.

A computational system 1000 (or processing unit) illustrated in FIG. 10 can be used to perform and/or control operation of any of the embodiments described herein. For example, the computational system 1000 can be used alone or in conjunction with other components. As another example, the computational system 1000 can be used to perform any calculation, solve any equation, perform any identification, and/or make any determination described here.

The computational system 1000 may include any or all of the hardware elements shown in the figure and described herein. The computational system 1200 may include hardware elements that can be electrically coupled via a bus 1005 (or may otherwise be in communication, as appropriate). The hardware elements can include one or more processors 1010, including, without limitation, one or more general-purpose processors and/or one or more special-purpose processors (such as digital signal processing chips, graphics acceleration chips, and/or the like); one or more input devices 1015, which can include, without limitation, a mouse, a keyboard, and/or the like; and one or more output devices 1020, which can include, without limitation, a display device, a printer, and/or the like.

The computational system 1000 may further include (and/or be in communication with) one or more storage devices 1025, which can include, without limitation, local and/or network-accessible storage and/or can include, without limitation, a disk drive, a drive array, an optical storage device, a solid-state storage device, such as random access memory ("RAM") and/or read-only memory ("ROM"), which can be programmable, flash-updatable, and/or the like. The computational system 1000 might also include a communications subsystem 1030, which can include, without limitation, a modem, a network card (wireless or wired), an infrared communication device, a wireless communication device, and/or chipset (such as a Bluetooth® device, a 802.6 device, a Wi-Fi device, a WiMAX device, cellular communication facilities, etc.), and/or the like. The communications subsystem 1030 may permit data to be exchanged with a network (such as the network described below, to name one example) and/or any other devices described herein. In many embodiments, the computational system 1000 will further include a working memory 1035, which can include a RAM or ROM device, as described above.

The computational system 1000 also can include software elements, shown as being currently located within the working memory 1035, including an operating system 1040 and/or other code, such as one or more application programs 1045, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 1025 described above.

In some cases, the storage medium might be incorporated within the computational system 1000 or in communication with the computational system 1000. In other embodiments, the storage medium might be separate from the computational system 1000 (e.g., a removable medium, such as a compact disc, etc.) and/or provided in an installation package, such that the storage medium can be used to program a general-purpose computer with the instructions/code stored thereon. These instructions might take the form of executable code, which is executable by the computational system 1000 and/or might take the form of source and/or installable code, which, upon compilation and/or installation on the computational system 1000 (e.g., using any of a variety of generally available compilers, installation programs, compression/decompression utilities, etc.), then takes the form of executable code.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art.

That which is claimed:

1. A method for measuring a photoplethysmograph (PPG) signal, the method comprising:
    capturing a plurality of frames of a subject with a color image sensor, wherein each of the plurality of frames includes a plurality of color channels for each pixel in the plurality of frames;
    tracking a position of a region of interest of the subject in each of the plurality of frames by determining a position of one or more points within the region of interest for each of the plurality of frames;
    creating a plurality of time series signals, each corresponding with a different one of the plurality of color channels of the plurality of frames and each data point of the each of the plurality of time series signals being associated with a frame of the plurality of frames;
    normalizing each of the plurality of time series signals in space to create a corresponding plurality of normalized time series signals, wherein normalizing each of the plurality of time series signals in space to create a corresponding one of the plurality of normalized time series signals comprises:
  determining a plurality of Euclidian distances between the position of a point within the region of interest within a given frame and each position of the point within the region of interest within each of a subset of frames of the plurality of frames;
  averaging the pixels of a corresponding color channel within the region of interest of the frames of the plurality of frames associated with a Euclidean distance that is less than a threshold Euclidean distance to create an averaged color channel value; and
  dividing a data value associated with the given frame of the plurality of frames by the averaged color channel value;
creating a spectral signal using the plurality of normalized time series signals; and
extracting the PPG signal from the spectral signal, wherein the PPG signal includes a pulse rate of the subject.

2. The method according to claim 1, further comprising:
correcting for blur artifacts associated with the PPG signal by removing motion artifacts from the spectral signal prior to extracting the PPG signal from the spectral signal.

3. The method according to claim 1, further comprising:
combining the plurality of normalized time series signals into a combined signal; and
filtering the combined signal to exclude signals having a frequency less than 30 BPM and greater than 250 BPM, wherein the filtered combined signal is used to create the spectral signal.

4. The method according to claim 1, wherein creating the plurality of time series signals comprises:
  creating a first time series signal of the plurality of time series signals, the first time series signal corresponding with a first color channel of the plurality of color channels of the plurality of frames, including, for each frame, averaging each of the pixels within the region of interest corresponding with the first color;
  creating a second time series signal of the plurality of time series signals, the second time series signal corresponding with a second color channel of the plurality of color channels of the plurality of frames, including, for each frame, averaging each of the pixels within the region of interest corresponding with a second color; and
  creating a third time series signal of the plurality of time series signals, the third time series signal corresponding with a third color channel of the plurality of color channels of the plurality of frames, including, for each frame, averaging each of the pixels within the region of interest corresponding with a third color.

5. The method according to claim 1, wherein extracting the PPG signal from the spectral signal further comprises excluding motion artifact signals from a combined signal that uses the plurality of normalized time series signals.

6. The method according to claim 1, further comprising:
measuring ambient light conditions;
determining an ambient light correction based on the ambient light conditions; and
correcting the plurality of time series signals using the ambient light correction.

7. A heart rate monitor comprising:
a camera;
an accelerometer; a memory; and
a processor electrically coupled with the camera, the accelerometer, and/or the memory, the processor configured to perform the method of claim 1.

8. The heart rate monitor according to claim 7, wherein:
the processor corrects for blur artifacts; and
the processor is further configured to remove motion artifacts from the spectral signal prior to extracting the PPG signal from the spectral signal.

9. The heart rate monitor according to claim 7, wherein the processor is further configured to:
combine the plurality of normalized time series signals into a combined signal; and
filter the combined signal to exclude signals having a frequency less than 30 BPM and greater than 250 BPM, wherein the filtered combined signal is used to create the spectral signal.

10. The heart rate monitor according to claim 7, wherein creating the plurality of time series signals comprises:
  creating a first time series signal of the plurality of time series signals, the first time series signal corresponding with a first color channel of the plurality of color channels of the plurality of frames, including, for each frame, averaging each of the pixels within the region of interest corresponding with the first color;
  creating a second time series signal of the plurality of time series signals, the second time series signal corresponding with a second color channel of the plurality of color channels of the plurality of frames, including, for each frame, averaging each of the pixels within the region of interest corresponding with the second color; and
  creating a third time series signal of the plurality of time series signals, the third time series signal corresponding with a third color channel of the plurality of color channels of the plurality of frames, including, for each frame, averaging each of the pixels within the region of interest corresponding with the third color.

11. The heart rate monitor according to claim 7, wherein when extracting the PPG signal from the spectral signal the processor is configured to exclude motion artifact signals from a combined signal that uses the plurality of normalized time series signals.

12. The method according to claim 7, wherein the processor is further configured to:
measure ambient light conditions;
determine an ambient light correction based on the ambient light conditions; and
correct the plurality of time series signals using the ambient light correction.

13. The method according to claim 1, further comprising, after extracting the PPG signal from the spectral signal:
determining acceleration data based in part on capturing the plurality of frames;
calculating a point spread function from the acceleration data; and
correcting for blur artifacts using the point spread function.

* * * * *